United States Patent
Brunner et al.

(10) Patent No.: US 10,092,211 B2
(45) Date of Patent: Oct. 9, 2018

(54) ELECTRODE SENSOR AND USE OF ELECTRODE SENSOR AS EIT ELECTRODE

(75) Inventors: Josef X. Brunner, Chur (CH); Pascal Gaggero, Bienne (CH)

(73) Assignee: SWISSTOM AG (CH)

( * ) Notice: Subject to any disclaimer, the term of this patent is extended or adjusted under 35 U.S.C. 154(b) by 837 days.

(21) Appl. No.: 13/810,661

(22) PCT Filed: Jul. 14, 2011

(86) PCT No.: PCT/CH2011/000165
§ 371 (c)(1),
(2), (4) Date: Jan. 16, 2013

(87) PCT Pub. No.: WO2012/006753
PCT Pub. Date: Jan. 19, 2012

(65) Prior Publication Data
US 2013/0116532 A1 May 9, 2013

(30) Foreign Application Priority Data

Jul. 16, 2010 (CH) ........................................ 1161/10

(51) Int. Cl.
*A61B 5/04* (2006.01)
*A61B 5/05* (2006.01)
(Continued)

(52) U.S. Cl.
CPC .......... *A61B 5/0536* (2013.01); *A61B 5/6804* (2013.01); *H01R 43/16* (2013.01);
(Continued)

(58) Field of Classification Search
CPC ... A61B 5/0536; A61B 18/1815; A61B 5/053; A61B 5/08; A61B 5/0537; A61B 5/0531; A61N 1/36014
(Continued)

(56) References Cited

U.S. PATENT DOCUMENTS

| 3,340,868 A | 9/1967 | Darling |
| 4,004,578 A | 1/1977 | Palmius |

(Continued)

FOREIGN PATENT DOCUMENTS

| BR | PI0704408 | 1/2009 |
| CN | 101180095 A | 5/2008 |

(Continued)

OTHER PUBLICATIONS

Costa, Eduardo L.V., (Feb. 2009) "Electrical impedance tomography." Current Opinion in Critical Care 15(1):18-24. Lippincott Williams & Wilkins, United States.

*Primary Examiner* — Joseph Stoklosa
*Assistant Examiner* — Brian M Antiskay
(74) *Attorney, Agent, or Firm* — Morriss O'Bryant Compagni Cannon, PLLC

(57) ABSTRACT

Electrode sensor comprising an array of spaced apart individual contact elements (27', 41), and an interface structure (30, 35) for forming contact between said contact elements and the skin; said interface structure comprising an interface layer of an essentially electrically insulating or poorly electrically conducting material (20', 29, 37) defining a skin (31) contact surface on one side and an array contact surface on the other side of the interface layer, a first pattern of an electrically conducting material on the array contact surface, a second pattern of an electrically conducting material on the skin contact surface, and electrical pathways (21', 39) connecting the first pattern with the second pattern; whereas, the first pattern comprises pattern elements, each individual contact element (27', 41) comprises a contacting surface area large enough to cover several pattern elements of said first pattern when contacting the array contact surface of the interface structure, and by contacting distinct sections of the first pattern with said individual contact elements, groups of electrical pathways establish contact further with distinct (Continued)

sections of the second pattern, so that an individual contact element (27', 41) defines an individual effective electrode on the skin contact surface. Method of manufacturing said electrode sensor, comprising the steps of: providing said interface structure, creating a first pattern of an electrically conducting material on its array contact surface, a second pattern of an electrically conducting material on its skin contact surface, electrically conducting pathways connecting the first pattern with the second pattern, and contacting sections of the electrically conducting first pattern with an array of spaced apart contact elements.

43 Claims, 6 Drawing Sheets

(51) Int. Cl.
*A61B 5/053* (2006.01)
*A61B 5/00* (2006.01)
*H01R 43/16* (2006.01)
*A61B 5/0408* (2006.01)

(52) U.S. Cl.
CPC ... *A61B 5/04085* (2013.01); *A61B 2562/0209* (2013.01); *A61B 2562/046* (2013.01); *A61B 2562/164* (2013.01); *Y10T 29/49204* (2015.01)

(58) Field of Classification Search
USPC ....... 600/372, 382, 384, 386–391, 393, 425, 600/508–509
See application file for complete search history.

(56) References Cited

U.S. PATENT DOCUMENTS

| | | | |
|---|---|---|---|
| 6,210,771 B1 | 4/2001 | Post et al. | |
| 7,315,754 B2 | 1/2008 | Leonhardt et al. | |
| 2003/0097878 A1 | 5/2003 | Farringdon et al. | |
| 2003/0212319 A1* | 11/2003 | Magill | A61B 5/0408 600/382 |
| 2004/0260167 A1* | 12/2004 | Leonhardt | A61B 5/0536 600/390 |
| 2005/0261564 A1* | 11/2005 | Ryu | A61B 5/6804 600/388 |
| 2006/0058600 A1* | 3/2006 | Eichler | A61B 5/0536 600/407 |
| 2006/0142654 A1 | 6/2006 | Rytky | |
| 2006/0211934 A1 | 9/2006 | Hassonjee et al. | |
| 2008/0183063 A1* | 7/2008 | Tang | A61B 5/0408 600/382 |
| 2008/0287770 A1* | 11/2008 | Kurzweil | A61B 5/0408 600/388 |
| 2008/0312522 A1* | 12/2008 | Rowlandson | A61B 5/04085 600/382 |
| 2010/0103112 A1 | 4/2010 | Yoo | |

FOREIGN PATENT DOCUMENTS

| | | |
|---|---|---|
| CN | 101188969 A | 5/2008 |
| CN | 101683263 A | 3/2010 |
| DE | 202006007226 U1 | 9/2007 |
| DE | 102008058375 A1 | 10/2009 |
| DE | 102008048984 A1 | 4/2010 |
| EP | 1016372 A1 | 7/2000 |
| EP | 1052485 A2 | 11/2000 |
| GB | 2350193 A | 11/2000 |
| JP | 3129292 | 2/2000 |
| JP | 2003144402 | 5/2003 |
| JP | 2005531386 | 10/2005 |
| WO | 199601077 A1 | 1/1996 |
| WO | 2003082104 A1 | 10/2003 |
| WO | 2006131855 A2 | 12/2006 |
| WO | 2008022482 A1 | 2/2008 |
| WO | 2010069023 A2 | 6/2010 |

* cited by examiner (a)

(b)

ELECTRODE SENSOR AND USE OF ELECTRODE SENSOR AS EIT ELECTRODE

CROSS-REFERENCE TO RELATED APPLICATIONS

This application is a national phase entry under 35 U.S.C. § 371 of PCT/CH2011/000165 filed Jul. 14, 2011, which claims priority to Swiss Patent Application No. 1161/10 filed Jul. 16, 2010, the entirety of each of which is incorporated by this reference.

BACKGROUND OF THE INVENTION

Technical Field

This invention relates to an electrode sensor for contacting the surface of the skin of a wearer to a plurality of electrodes, in particular for the use for electrical impedance tomography (EIT). An Electrode sensor comprises a plurality of electrode contact elements. Each of said electrode contact elements individually contacts the skin of a test person and allows the application or measurement of potential and/or current locally in order to establish and measure an electrical field within a living being.

This invention relates to a means and a method for establishing reliable and stable electrical contact between the electronic part of an electrical impedance tomography device and the skin of a living being.

Background

Electrical impedance tomography (EIT) is a known technique. More details about this technique can be found in "Electrical impedance tomography" by Costa E L, Lima R G, Amato M B, Curr Opin Crit Care. 2009 February; 15 (1):18-24, which is incorporated herein by reference. For intensive care doctors, pulmonologists, physiotherapists and high performance athletes electrical impedance tomography (EIT) is an imaging method that provides real-time information about regional lung ventilation and perfusion (flow or pulsatility of blood). In contrast to conventional methods, EIT does not require the patient to breathe through a sensor, does not apply ionizing x-rays and can be used for extended periods, say 24 hours or even longer. Therefore, EIT can be used continuously and is therefore suited for monitoring treatment and training effects in real time and along the time. EIT was first used to monitor respiratory function in 1983 and remains the only bedside method that allows continuous, noninvasive measurements of regional changes in lung volumes.

In EIT, an electrical current is applied to the skin of the thorax to establish an electrical field within the thorax. Typically, 8, 16 or 32 electrodes are placed around the thorax and used to measure the electrical potentials resulting from the field. The measured voltages are used to estimate the distribution of electrical impedance within the thorax using algorithms specifically developed for ill-posed non-linear problems. In order to overcome the ill-posed nature of impedance estimation, most EIT imaging algorithms make use of additional assumptions, known as regularizations, such as smoothness of the intra-thoracic impedance distribution or a-priory information. These regularizations help the mathematical algorithm to decide between competing solutions, producing an image that is a reasonable estimation of the true impedance distribution within the thorax, at the expense of degraded spatial resolution or attenuation of maximum perturbations. Image creation software typically implements regularizations with different methods and such software is known in the art.

Finally, the calculated impedance-distribution is converted into an image that shows presence, absence or changes of gas and if desired also blood content. Plotted rapidly in sequence, like a movie, these images create a representation of gas and blood flowing in and out of each lung region and allow the doctor or athlete to evaluate lung function in real-time. Instead of plotting images, characteristic features can be extracted from the image and displayed as numbers or indices. Examples are: left vs. right ventilation or dorsal vs. ventral ventilation where these numbers represent a percentage of total ventilation.

The shape as well as the composition of the thoracic wall can contribute as much to the measured voltages at the chest wall surface as internal thoracic impedances. Consequently, the reconstruction of the absolute impedance distribution, albeit feasible, requires knowledge of the shape of the thorax as well as the impedance between the electrode and the skin.

Difference images, as first described by Barber and Brown, however can be generated without prior knowledge of the thoracic structure. They are generated from changes in impedance relative to a baseline or reference condition, assuming that both, the shape of the thorax as well as the contact impedances do not change significantly between these conditions. This relative or differential approach cancels out most errors related to incorrect assumptions about thoracic shapes, electrode position, body composition and contact impedances not only theoretically, but also in patients since this same error applies to both images in the same way. Most currently available EIT devices in clinical practice and most publications in the field use this relative approach. Thus, they display changes in impedance and not its absolute value. However, this perceived limitation is not a real problem if the dynamics of organ functions such as the beating heart and breathing lungs are to be monitored.

However, even the use of relative EIT in clinical practice is not possible unless the contact impedance between electrodes and body skin become predictably stable over time. Any significant change of contact impedance will erroneously be perceived as changes within the organs of interest. Thus, even though the precise absolute value of the contact impedance at the site of each electrode does not need to be known, the condition that these values have to remain stable over time has yet to be fulfilled if meaningful EIT images are to be created by the image creation software.

Furthermore, it is highly desirable to not only achieve stable but also rather low contact impedances so as to make maximal use of the limited amount of current (10 mAmps) that is allowed to be injected into the living being. Only such currents achieve a maximal signal to noise ratio. When reconstructing images, traditional EIT algorithms assume that the electrodes (usually 8, 16 or 32) are located at discrete physical locations around the chest, most often in an equidistantly spaced fashion. They do not take crosstalk between such electrodes into account. Crosstalk and changes in crosstalk can be interpreted by the image creation software as a signal stemming from internal organs and functions of these organs. Thus, crosstalk between electrodes should remain low and constant.

Yet another aspect to be considered when designing any device or structure to be placed in direct contact with the skin of a living being is its physical impact on such skin, which may lead not only to a physical irritation or even breakdown of the skin but also of the underlying tissues such as muscles, tendons or bones (decubitus). The key contributing factors in the pathogenesis of such breakdown are: 1) Acute critical or chronic illness of patient (intrinsic factors) 2) The local absolute pressure (usually >30 mmHg) compressing the small blood vessels and capillaries (this is usually the highest in areas where bones are located close to the body surface) and/or the pressure relative to the one perfusing the tissue, 3) the time such pressures are applied and 4) the time-pressure-product (even very high pressures can be tolerated for short periods of time). Furthermore, elevated 5) moisture and 6) temperature levels with increased metabolic demand make the tissue susceptible to damage. In addition, 7) shear stress (forces tangential to the tissue surface) exert their negative effects mainly in the capillary region where they lead to a kinking of such vessels preventing oxygen and nutrient rich blood from flowing to the site of utilization (ischemia).

This lack of nutrients and oxygen on the one hand and the accumulation of CO2 and metabolic byproducts as well as the pooling of venous blood together with the progressive acidification of the local tissue on the other hand initially cause swelling and finally demise of the cells (necrosis). Pressure sores can be classified according to dimension and severity, the latter ranging from a localized but irreversible redness of the skin to a complete destruction of the underlying tissues including the bones.

In the context of the above, it becomes obvious that any physical structure applied to the fragile skin of living subjects needs to accommodate the individual needs of such subjects, especially those of their skin and supportive tissues. Such needs preclude the use of any simple physical structure that prevents the skin from breathing and from exchanging moisture and heat. Furthermore, the structure may neither exert excessive tangential stress nor local pressures above the tissue perfusion pressure.

Traditional EIT systems use isolated gel electrodes i.e. the ones typically used in ECG applications, where these electrodes are connected by individual passive or actively shielded cables to remotely located electronic circuits. In clinical practice, a set of 8, 16 or 32 of these isolated electrodes with their respective connecting cables are not only impossible to apply to the thorax of supine patients—the type of patient who would benefit from EIT the most—but they do not comply with the essential requirement of a stable contact impedance over time. When in contact with the warm and moist skin of a patient these gel-based electrodes may change their electrical characteristics quite drastically. A patient's body movement in conjunction with the varying mechanical forces exerted by the set of cables will move individual electrodes away from their original point of attachment. Furthermore, these same forces will change their physical contact with the skin in an unpredictable manner.

The individual cables used by traditional EIT systems to carry the injection currents and voltage signals over long (usually >2 m) distances typically have unknown impedance and capacity values but worse, they interact with each other, thereby influencing measured signals by an unknown magnitude and direction. These changes disturb the EIT images just like the changes in contact impedance and crosstalk.

In an attempt to overcome these typical limitations of traditional EIT systems, such systems are being miniaturized in such a way that active electronic circuits are located right at the site of current injection and voltage measurements. While such an approach increases the overall signal quality by not only removing the electrical but also the mechanical problems encountered when using long analog cables, it does not solve the problem of variable contact impedances and electrode crosstalk.

For the reasons described above, there is a clear need for methods and means to achieve a more reliable and stable electrical contact between the electronics of EIT systems and the skin of a living being. At the same time any potential solution must be producible in large quantities and at low costs, especially when designed to be used as typical single patient use disposable items.

Known solutions, such as the one given in U.S. Pat. No. 7,315,754, are based on the idea that an array of spatially separated individual electrodes can best be placed on the body surface if they are embodied with a mechanical structure joining them together i.e. in the form of a belt- or garment-like structure. While each one of the electrodes is made of electrically conductive material, the mechanical support structure linking them mechanically must not be made of electrically highly conductive materials (i.e. not made of materials with conductivities in the range of metals) since this would cause short circuits or at least enhance crosstalk between electrodes. Despite the elaborate construction of known electrode supporting structures, they lack good electrical contact properties in combination with good wearing properties. Furthermore, commercially produced electrode supporting structures are expensive. Thus, acceptance of patient and test person and/or medical staff is usually low. Alternatively, placing and fixing conductive electrodes together with their electrical line connections individually onto a mechanical support structure is cumbersome, expensive and might not yield the high electrical and mechanical reliability needed for EIT-based monitoring purposes in the clinical environment.

Document WO2010/069023 discloses an electrode system, which is useful in the EIT technology. Contact between skin and measurement instrument is established at a multitude of locations where pairs of layers of electrically conductive adhesive materials contact each other mutually through pores of a non-conducting layer of a blade. Said material may be a gel. Half of said layers—arranged on one side of the blade—are in direct contact with the skin, while the other half of said layers—arranged on the other side of the blade—is contacted by the measurement instrument. Location and size of areas where the pairs of layers establish electrical contact are predetermined during the manufacturing process. Consequently, the location for attaching a plurality of electrical conductors is predetermined and fixed.

Document U.S. Pat. No. 6,210,771 discloses fabrics used as integral elements of electrical circuitry. Hereby, fabrics serve as substrates onto which electrical components are connected or as the electrical components themselves.

Patent application WO 2008/022482 A1 discloses a textile electrode device having two layers of textile. The first textile layer—designed to bias the body of an individual wearing the device—is provided with a group of embroidered electrodes. Each embroidered electrode is formed from an electrically conductive yarn and connected to an associated electrical supply line. The supply lines are designed as embroidered conductor tracks on the second textile layer only. Said second textile layer is arranged on the side of the first textile layer which faces away from the body. Each embroidered electrode is connected fixedly with the associated supply line. Connection of electrode patch and supply line is established in that the electrode pattern is stitched through both textile layers. For example the conductive yarn is used to sew up the two layers at the positions of the electrodes. Thus, design and position of each electrode is determined by the embroidered pattern. Each electrode patch with its supply line forms an electrically coherent conductive design. Supply lines may be designed such that they can be electrically contacted with a ribbon plug connector.

Utility model DE20 2006 007 226 U1 discloses a textile pixel electrode having two plane textile structures. First and second structures are arranged in parallel in a distance to each other; the first structure serving for contacting the skin of a wearer and the second one pointing away from the wearer's skin. The first structure comprises at least one electrode pixel which is formed from one electrically conductive yarn. The second structure is elastically deformable. Each pixel may be activated or addressed individually or alternatively several pixels are activated in groups by an electronic unit, i.e. a multiplexer. Which pixels actually are addressed is determined within the electronic unit. The electronic unit or multiplexer may be attached to or integrated into the second textile structure.

From a production standpoint therefore it is highly desirable to create a single structure which serves both, the electrical (discrete areas of conductivity) and mechanical (continuous mechanical structure) requirements and may be produced at a low price at the same time.

The present invention provides of a reliable and stable electrical contact between electronic measuring equipment, in particular the electronic part of an electrical impedance tomography device, and the skin of a living being, e.g. a test person or patient. Furthermore, the present invention provides a new and improved electrical patient interface for electrical impedance tomography which minimizes shear forces within the skin and high pressures on and within the skin and thus prevents injury such as pressure ulcers. The present invention further provides a electrical contact to the skin while at the same time avoiding cross-talk between electrodes even if the patient is moving or the electrodes are moved. The present invention further provides a solution that is producible at low cost, particularly for single-patient use products.

SUMMARY OF THE INVENTION

The present invention provides an electrode sensor comprising
(a) an array of spaced apart individual contact elements, and
(b) an interface structure for forming contact between said contact elements and the skin;
said interface structure comprises
an interface layer of an essentially electrically insulating or poorly electrically conducting material defining a skin contact surface on one side and an array contact surface on the other side of the interface layer,
a first pattern of an electrically conducting material on the array contact surface,
a second pattern of an electrically conducting material on the skin contact surface, and
electrical pathways connecting the first pattern with the second pattern; and is characterized in that,
the first pattern comprises pattern elements,
each individual contact element comprises a contacting surface area, which covers several pattern elements of said first pattern when contacting the array contact surface of the interface structure, and
by contacting distinct sections of the first pattern with said individual contact elements, groups of electrical pathways establish contact further with distinct sections of the second pattern, so that an individual contact element defines an individual effective electrode on the skin contact surface.

Said electrode sensor may also be called electrode sensor array, since it contains an array of contact elements.

Thus, the skin contacting area of the inventive electrode sensor is divided into areas that are either conductive or non-conductive, whereby only those of the conductive pathways become electrically active and assume a functionality as electrical connector, which are in direct contact with the skin on one side and with one of the contact elements of the array for the electronic parts on the other side. The physical dimensions of each one of the conductive pathways and the non-conductive spaces surrounding them are usually smaller than the extension of the contact elements. More than one or even many conductive pathways may form effectively one single electrical contact between one contact element and the skin surface. More specifically, at least three electrical, or at least 10, or at least 50 pathways per electrode are present. The conducting material of the patterns and the electrical pathways are well conducting in comparison to the above-mentioned essentially electrically insulating or poorly electrically conducting material.

In one embodiment the second pattern of the interface structure comprises pattern elements.

Advantageously, an electrode sensor of the present invention is provided, wherein
the first pattern of an electrically conducting material on the array contact surface comprises pattern elements, such as e.g. dots, lines, spots and/or patches and
the second pattern of an electrically conducting material on the skin contact surface comprises pattern elements, such as e.g. dots, lines, spots and/or patches, and
the electrical pathways connect pattern elements of the first pattern with pattern elements of the second pattern.

In another embodiment, the pattern elements of a pattern are mutually electrically isolated; thus a pattern is electrically incoherent. The electrical pathways connect individual pattern elements of the first pattern with individual pattern elements of the second pattern.

In yet another embodiment, each individual contact element comprises a contacting surface area, which covers several pattern elements (i.e. many dots, lines, spots and/or patches) of said first pattern when contacting the array contact surface of the interface structure, so that by contacting distinct sections of the first pattern with said individual contact elements, groups of electrical pathways establish contact with distinct sections of the second pattern, so that each individual contact element defines an individual effective electrode on the skin contact surface.

The interface structure is a cost effective intermediate for protecting and contacting the skin with an array of spaced apart individual contact elements. Of particular advantage is the fact, that the array may be arranged randomly on the interface structure, because each individual contact element comprises a contacting surface area, which when contacting the array contact surface of the interface structure covers many dots, lines, spots and/or patches of said first pattern. Thus the relatively big dimension of the contact elements in comparison to the small dots, lines, spots and/or patches of said first pattern allows contacting several or many pathways at the time and independent of the location on the array contact surface of the interface structure.

In still another embodiment the first and/or the second patterns are incoherent patterns, in particular incoherent patterns of e.g. electrically conductive spots, dots, patches and/or lines. This means that distinct elements of a pattern, such as spots, dots, patches and/or lines, are electrically isolated from each other. Thus, the term distinct herein has the meaning of electrically isolated.

Since the spots, dots, patches and/or lines on a surface predominantly are electrically isolated from each other, the mentioned pattern is electrically incoherent. However, pattern elements such as spots, dots, patches and/or lines of the first pattern on one surface are individually connected with pattern elements such as spots, dots, patches and/or lines of the second pattern on the other surface. An individual connection between a spot, dot, patch or line of the first pattern and a spot, dot, patch or line of the second pattern is established by a pathway. Advantageously pathways are electrically isolated from each other, i.e. are electrically mutually isolated. Alternatively, an individual connection between a group of spots, dots, patches or lines of the first pattern and a spot, dot, patch, line or a group of spots, dots, patches or lines of the second pattern is established by a branched pathway, i.e. a group of interconnected pathways. Furthermore alternatively, an individual connection between a group of pattern elements such as spots, dots, patches or lines of the second pattern and a pattern element such as a spot, dot, patch, line or a group of pattern elements such as a group of spots, dots, patches or lines of the first pattern is established by a branched pathway, i.e. a group of interconnected pathways.

In yet another embodiment the electrode sensor is characterised in that each pattern is composed of a multitude of individual (i.e. electrically mutually isolated) pattern elements, such as dots, lines, spots and/or patches. The pattern elements on the array contact surface are thus electrically isolated from one another. Moreover, pattern elements on the skin contact surface are electrically isolated from one another.

In still another embodiment multitude of pattern elements of a pattern (i.e. the first or the second pattern) comprises at least three pattern elements, at least five pattern elements, or at least ten pattern elements.

Furthermore, in still another embodiment the electrode sensor is characterised in that electrical pathways connecting the first pattern with the second pattern connect individual dots, lines spots, patches and/or a group thereof of the first pattern with individual dots, lines, spots, patches and/or a group thereof of the second pattern.

Actually, size and shape of the individual effective electrode on the skin contact surface depend on the size and shape of the individual contact element. For example where the pathways connect the two essentially parallel surfaces of the interface structure with lines essentially orthogonal to said surfaces, size and shape of the contact area of an individual contact element with the interface structure is transmitted onto the skin contacting surface to form the effective electrode. Thus contact area and effective electrode may have similar shape, contour and dimension. However, the conductive pattern forming the effective electrode may be composed of an incoherent pattern of electrically conductive dots, patches and/or lines.

Advantageously, the array of spaced apart individual contact elements is detachably fixable to the array contact surface.

In another embodiment, the first and the second patterns are arrangements (homogeneous arrangements) of randomly or regularly distributed pattern elements. From this follows that dimension and shape of the individual effective electrodes is substantially defined by and substantially corresponds to the dimension and shape of the individual contact elements.

In yet another embodiment, the pathways connect pattern elements which substantially are situated face-to-face with each other on opposite sides of the interface layer. From this follows that the location of the individual effective electrodes on one side of the interface layer substantially is defined by and corresponds to the location of the individual contact elements on the opposite side of the interface layer. In another embodiment, an effective electrode area is shifted with regard to the location of its corresponding contact element by not more than 10 mm, or not more than 5 mm, or not more than 2 mm, in any direction parallel to the skin contacting surface. Advantageous effects of said electrode sensor are linked to its construction in two parts involving an interface structure and an array of contact elements. During use of the sensor the two parts need to be attached to each other in order to ensure electrical contact. The two parts can be physically linked in a permanent manner and thus are discharged together when e.g. any of the parts is worn out or unhygienic. For certain uses, such as in situations of intensive medical care, a wholly or partially disposable sensor might be preferable. In certain situations it might be desirable that the two parts are detachable from each other, in order to either dispose one of the parts, e.g. when worn out or broken, or remove one of the two parts temporary while not in use. Exemplarily, during the analysis of athletes the array of contact elements may be temporarily removed from a garment-type interface structure. In another example the interface structure, which in operation was in contact with the skin of a patient or tested person, may be disposed and replaced with a new one after use. Alternatively the interface part is washed and re-attached for reuse. Due to direct contact with the skin said interface layer gets contaminated and for hygienic reasons should not be used to analyze further patients or test persons. The interface structure can be manufactured relatively cheaply. The array of contact elements however is reusable. Said array comprises spaced apart individual contact elements (e.g. EIT-chips), which may be electrically connected through a bus system and optionally further supported by a support structure. The disposable interface structure and the reusable array form a user friendly electrode sensor for EIT-measurements for use in hospitals, research institutes as well as private homes. The interface structure may be formed as belt or strip; however, it is possible to design the interface structure as a garment or integrate it into a garment. Such designs may find best use in EIT tests of athletes or patients in movement.

The electrode sensor is composed of at least two detachable parts. One part is the array of spaced apart individual contact elements. The other part is the interface structure for forming contact between the contact elements and the skin.

In yet another embodiment, an individual effective electrode is defined by the selection of the pathways by a contact element on the interface structure. Thus, each contact element contacts a certain group of pathways, whereby these pathways lead to a skin contact area where the contact between pathway and skin is established.

Advantageously an individual contact element defines at least one dimension of an individual effective electrode, i.e. the width or length, of an individual effective electrode. For example in one embodiment an array of contact elements is spread along the longitudinal extension of a strip-like non-conductive material. Each contact element connects to a group of parallel conductive lines which perpetuate—starting from the array contacting side—into and in the plane of skin contact. Advantageously said conductive lines are arranged in essentially orthogonal direction to the longitudinal extension of the strip. In the plane of skin contact each group of parallel lines covers a certain area of which the width (or length) is delimited by the size of the corresponding contact element. The width of each conductive line may be one of a conductive yarn or yarn compound when interface structures are fabricated from e.g. woven or knitted material. However, especially where printing techniques are employed for fabricating the conductive lines various shapes and dimensions are possible.

Alternatively an individual contact element defines two dimensions of an individual effective electrode, i.e. the area, of an individual effective electrode. For example in another embodiment an array of contact elements is spread along the longitudinal extension of a strip-like non-conductive material. Each contact element connects to a group of conductive lines which penetrate—starting from the array contacting side—through the strip-like non-conductive material to emerge at the plane of skin contact. In the plane of skin contact each group of emerging conductive lines covers a certain area which is actually delimited by the size and shape of the corresponding contact element. In a simple embodiment the first and second conducting patterns form dot patterns, meaning that the pathways at their emerging ends form a conductive dot. Other, more elaborate patterns are possible. For example the diameter of the dot may be enlarged in comparison to the one of the pathway in order to increase the electrical contact between interface structure and contact elements and/or interface structure and skin.

In principle a single electrical pathway leading from a contact element to the plane of skin contact suffices for establishing an electrical contact. However, advantageously for forming an individual effective electrode a contact element is connected to a plurality of electrical pathways. This ensures reliable contact and passage of current even when some of the pathways are defect.

In still another embodiment, the electrically conducting first pattern, the electrical conducting second pattern and the electrical pathways of the interface structure are designed such that, by contacting the interface structure with a contact element, the area of contact on the array contact surface defines essentially the area of an effective individual electrode on the skin contact surface.

In yet another embodiment, the contact elements are mounted to a support structure, whereby said support structure and said interface structure are releasably fastened to each other. A releasable connection may be established by a hook-and-loop tape (e.g. a Velcro fastening) or other releasable fastenings. Alternatively, non-releasable connections are possible, such as e.g. heat-sealed connections.

In another embodiment, the electrically conducting first pattern is formed by spaced apart electrically conducting lines on the array contact surface, which lines are individually electrically connected via the pathways with distinct sections, spots or lines of the second pattern. A section of a pattern defines a subset of spots, dots, lines and/or patches of a pattern (i.e. a subset of pattern elements); thus a section of a pattern includes at least two spots, dots, lines or patches or at least a combination of any two elements of a group consisting of spots, dots, lines and patches.

In another embodiment, the electrically conducting second pattern is formed by spaced apart electrically conducting lines on the skin contact surface whereas a plurality of said lines forms an individual effective electrode.

In still another embodiment, the electrically conducting first pattern is formed by spaced apart electrically conducting spots on the array contact surface, which spots are individually electrically connected via the pathways with distinct sections, spots or lines of the second pattern.

In yet another embodiment, the electrically conducting second pattern is formed by spaced apart electrically conducting spots on the skin contact surface whereas a plurality of said spots forms an individual effective electrode.

In still another embodiment, the electrically conducting second pattern is formed by an essentially continuous zone of electrically conducting material on the skin contact surface whereas a section of said material forms an individual effective electrode. Thus, although the second pattern covers all or most of the skin contact surface, only certain areas on said second pattern form individual effective electrodes. The reason is that by contacting distinct first areas on the first pattern with the contact elements of the array, only corresponding second areas on the second pattern (i.e. areas of the second pattern that are electrically connected to said first areas) form individual effective electrodes.

Alternatively the electrically conducting first pattern is electrically connected with the second pattern by electrically conducting pathways extending essentially orthogonally from the array contact surface to the skin contact surface of the interface layer. Hereby the conducting pathways penetrate the interface layer of an essentially electrically insulating or poorly electrically conducting material. Thus, the first and second pattern and the pathways form together a three-dimensional pattern (i.e. a volume pattern).

In another embodiment, the electrically conducting first and second pattern and the electrically conducting pathways form together a volume pattern (i.e. a three-dimensional pattern) extending from the skin contact surface to the array contact surface.

In yet another embodiment, the electrically conducting first pattern of the array contact surface is electrically connected with the second pattern of the skin contact surface by electrically conducting pathways extending around a lateral edge of the essentially electrically insulating or poorly electrically conducting material and around an optional, non-conducting core material. Hereby, the interface layer of the essentially electrically insulating or poorly electrically conducting material is folded along the lateral edge. Due to folding a lateral bend is formed. Thus, the first pattern and the second pattern are situated on the two exterior surfaces facing opposite directions. The two patterns are electrically connected by electrical lines directed along the surface around the bend.

In yet another embodiment, the electrically conducting first pattern, the electrically conducting second pattern and the electrically conducting pathways are formed from the same material.

In still another embodiment, the electrically conducting first pattern, the electrically conducting second pattern and the electrically conducting pathways are integral with the interface layer. First pattern, second pattern, pathways and interface layer form the interface structure. This interface structure may be designed as disposable and manufactured relatively cheaply.

Advantageously the electrical pathways are spaced apart from each other, i.e. electrically mutually isolated. Thus, e.g. the pathways can be spaced apart when situated on the surface of the interface layer and/or they can be separated by non-conducting material when penetrating the bulk of the interface layer.

Advantageously groups of electrical pathways establishing contact with distinct sections of first and second patterns are spaced apart from each other, i.e. electrically mutually isolated. For example groups of electrical pathways are spaced apart more distant from each other than the single pathways forming said group.

In another embodiment, the support structure forms a flexible belt-like structure. A flexible structure adapts to the body part where it is affixed and is comfortable for the wearer. The support structure may be flexible and elastic. Hereby movement and breathing are not obstructed, in particular when fixed around the chest of a living being.

In another embodiment, the interface layer and thus the interface structure is manufactured from foams, woven, knitted or non-woven fabrics. Such materials allow transpiration and therefore are comfortable to wear.

In another embodiment, the first pattern, the second pattern and the pathways comprise electrically conductive paint or particulate material, which may be applied by sputtering or printing, in particular micro-printing.

Alternatively, the first pattern, the second pattern and the pathways comprise electrically conductive yarn, wire or fibers, which are for example woven, knitted or stitched into the interface structure.

In another embodiment, the interface structure is manufactured from a foam material comprising a plurality of non-compressed areas, which have a first electrical conductivity, and compressed areas, which have a second electrical conductivity, whereby the second electrical conductivity is higher than the first electrical conductivity.

The electrode sensor may be provided in the form of a kit. Advantageously such a kit comprises components which can be assembled by the user. For example a useful and suitable kit may comprise the following two components (a) and (b):

(a) an array of spaced apart individual contact elements, and
(b) an interface structure for forming contact between said contact elements and the skin;
  the interface structure comprising
    an interface layer of an essentially electrically insulating or poorly electrically conducting material defining a skin contact surface on one side and an array contact surface on the other side of the interface layer,
    a first pattern of an electrically conducting material on the array contact surface,
    a second pattern of an electrically conducting material on the skin contact surface, and
    electrical pathways connecting the first pattern with the second pattern; whereby the kit advantageously is characterized in that or designed such that,
  the first pattern comprises pattern elements (and optionally the second pattern also comprises pattern elements),
  each individual contact element comprises a contacting surface area, which is suitable to cover several pattern elements of said first pattern when contacting the array contact surface of the interface structure, and
  by contacting distinct sections of the first pattern with said individual contact elements, groups of electrical pathways establish contact further with distinct sections of the second pattern, so that an individual contact element can define an individual effective electrode on the skin contact surface.

After assembling the at least two components of the kit the electrode sensor may be used to carry out electrical measurements.

Respective advantageous and/or alternative features of the electrode sensor may also apply to the electrode sensor kit.

The inventive method of manufacturing an electrode sensor, comprises an array of spaced apart contact elements and an interface structure for forming contact between said contact elements and the skin, comprising the steps of:

providing an interface structure in the form of a layer of an essentially electrically insulating or poorly electrically conducting material defining a skin contact surface on one side and an array contact surface on the other side of the interface layer,
  creating a first pattern of an electrically conducting material on the array contact surface,
  creating a second pattern of an electrically conducting material on the skin contact surface, and
  creating electrically conducting pathways connecting the first pattern with the second pattern,
  contacting sections of the electrically conducting first pattern with an array of spaced apart contact elements.

This manufacturing method is particularly advantageous because array and interface structure can be manufactured separately and according to their specific use. For example design requirements of interface structures for measurements in an intensive care setting or athlete surveying setting differ. Specially adapted interface structures may be combined with the same array depending on the condition of the patient or test person. Moreover, for the purpose of a measurement various array designs may be combined with various interface structure.

In another embodiment, the first and second pattern and the pathways are manufactured by providing or inserting spots and/or lines of electrically conducting material in the interface structure, which penetrate the interface layer from the skin contact surface to the array contact surface.

In another embodiment, the contact elements are mounted or fixed on a support structure. The support structure may align the contact elements in an array and determines mutual distance and position. The support structure gives mechanical stability and ensures electrical interconnection between the contact elements of the array and the interface structure. The support structure may be present, where the interface structure and the array of contact elements are designed as two detachable parts. For use of the electrode sensor the interface structure and said support structure comprising the contact elements are connected with each other. During use of the sensor interface structure and electrode elements are in physical and electrical contact with each other.

Advantageous for use are electrode sensors which are disposable. The interface structure with the interface layer, the electrically conducting first pattern, the electrically conducting second pattern and the electrically conducting pathways may be designed as a disposable.

The herein described electrode sensor may be used for medical monitoring and may be of assistance in diagnosis. The electrode sensor is useful for applying and measuring an electrical field on a living being. In particular it is used to conduct electrical impedance tomography (EIT) measurements. Moreover, it is a noninvasive method for analyzing living beings.

The inventive solution is described in more detail in the following embodiments and examples.

The function of above-mentioned interface structure can be accomplished by means of various embodiments. Here several exemplary embodiments are described. Combinations thereof may serve to further optimize for specific needs.

One embodiment of the invention uses biocompatible corrugated segmentally compressed electrically conductive foam strips. The segmental structure of the foam strips may be permanently compressed e.g. induced during the manufacture of the foam strip. Alternatively, foam strips which are wholly compressed, i.e. which are equally strongly compressed at all locations, may be used. In order to avoid crosstalk, the electrical resistance of the non-compressed foam should be similar to the one of the human skin (in the range of 50 to 1000 Ohm) or above, such as for example in a range above 1000 Ohm or even above 10000 Ohm, but certainly not below the resistance of human skin. While the compressed dense and thus higher conductive thin parts of said structure, which are on their front side in contact with the skin and on their back side in physical and electrical contact with the electronics, act as the actual low-impedance electrode through which currents are injected and voltages are measured, the non-compressed less conductive foamy parts in contact with the skin but not in direct contact with said electronics act as absolute or relative electrical isolators or resistors between adjacent conductors or electrodes. While the non-compressed segments do not conduct electrical currents well, they contribute significantly to mechanical stability, stretchability and padding. The conductive foamy materials are not only compressed at chosen locations for electrical reasons but can also be deformed to accommodate the specific needs of particular anatomical areas such as a female breast. If a foam strip material is used which is not at all compressed or which is compressed to the same extent over its entire elongation, in order to avoid crosstalk the conductivity of the foam material may be in the vicinity of the one for skin, and may be the conductivity is either equal or lower than the conductivity of skin. Furthermore, the invention can also be realized on the basis of primarily electrically non-conductive foam (e.g. PE or PU), which is made electrically conductive by coating or impregnating with a conductive substance such as e.g. carbon. In this instance it may be advantageous to render the foam material conductive only in those segments, which shall act as conductors.

In general, reticulate foams are used advantageously. Reticulate foams which are permeable to gas and liquid ensure a certain breathability of the material and therefore allow for normal transpiration of the skin even in areas of electrical contact.

Another embodiment of the invention is made of woven or knitted textiles to create separate conductive pathways in a classical "double-rip-like" fashion typically found in underwear. Selected segments are made of electrically conductive yarns and where the elevated parts make contact with the skin and the adjacent valleys establish contact with the electronics on the other side of the textile thereby comprising the electrically conductive pathway through the textile. These conductive parts are systematically separated by non-conductive spacer segments of similar or different textile structure thereby electrically isolating neighboring conductive parts from each other. When used in conjunction with electronics, the size of the electrically functional area of each electrode and thus the actual area of each one of the patient interfaces is defined by the amount and length of conductive elements being in direct contact with both, the skin on the one side and the connecting part of the electronics on the other.

Another embodiment of the invention is made of a breathable three-dimensional knitted spacer fabric comprising conductive pathways leading through the thickness from one surface side of the fabric to the other one. The basic principle of a spacer fabric is its combination of outer textile surfaces and an inner structure formed by a so called spacer yarn connecting the two outer layers while at the same time establishing a certain distance. Pathways may be made of additional electrically conductive yarns electrically connecting the two surface sides and preferably connecting individual electrical contact areas or contact spots on each surface side with one another. The individual electrical contact areas or contact spots on each surface may for example be formed from the same yarn forming the pathways or imprinted conductive patterns.

Another embodiment of this invention can be realized by printing, micro-printing or sputtering onto the front side of a woven or non-woven fabric as mechanical carrier material distinct conductive pathways or dots made of electrically conductive inks or polymers. These inks or polymers leak locally into and through the fabric in such a way that the conductive spot penetrates through its back side. This way, non-connected separate electrically conductive pathways ranging from the front side to the back side of the fabric are created. The particular advantage of such a printed, micro-printed or sputtered approach is the fact that large areas or even entire textile batches can be equipped this way leading to extremely low production costs. If micro-printing is used, the spatial resolution as well as the amount of conductive paths can be maximized and yet the desired and known advantages of textiles or fabrics—especially their breathability—can be preserved. Such printed conductive path could be used to produce T-shirts having printed zones of the above kind in areas of particular interest such as the heart and lung regions.

Another embodiment of this invention is realized by embroidering, stitching or sowing spatially separated individual conductive paths, which are electrically isolated from each other, through carrier materials of any kind.

Yet another embodiment of the above invention is made of non-woven or woven elastic or non-elastic fabric with electrically conductive wires attached to one side of it in a parallel fashion at predefined distances but vertical to the main direction of stretchability. Hereby the direction of stretchability corresponds to the circumference direction of a body part to be analyzed. These electrically non-insulated conductive wires create electrical pathways which are in no direct contact with one another. These individual conductive pathways are systematically separated by sufficient distance so as not to create cross talk between them. One end of a set of wires is connected to the electronics of each electrode, whereby the amount of wires used in such a connection determines the electrically functional width of each electrode and thus the actual segment of each one of the patient interfaces. While the amount of wires being in direct contact with both, the skin on the one side and the connecting part of the electronics on the other determines the width, the length of wires in direct contact with the skin multiplied by the respective width finally determines the effective area acting as electrode. Such an electrode design can be obtained by folding or wrapping the above materials around a core of non-conductive fabric or padding material like foam in such a way that the electronic contacts are positioned just opposite the zone of skin contact.

Further embodiments result from combinations of above-presented embodiments. For this purpose the electrical pathways of two different fabrics could be electrically contacted by forming a layered composite, thus forming a double layered interface structure, where one type of fabric is used as the skin contacting side and another type of fabric is used as the electrode array contacting side. For example by forming a two layer interface structure combining an electrically conductive foam strip (as the skin contacting side) with a knitted spacer fabric (as the electrode contacting side), optimal electrode contacting properties and comfort for the wearer, respectively, can be achieved.

The invention is used to make contact between one or several electrodes, typically an array of electrodes, and skin in living beings, particularly humans. The advantage of the invention is that the electrodes do not touch the skin directly but via a layer of fabric, foam or tissue which prevents or dissipates friction, pressure and shear forces on and within the skin. An advantage when using foams, fabrics and tissues is based on the non-occlusive nature of the materials. Transpiration during EIT examination is to a large extent ensured due to the permeability of the materials to gas and liquid. A further advantage is that there is always a defined pathway to the skin, even if the electrodes are moving on the layer of fabric, foam or tissue, or the electrodes are being moved by body movement. A further advantage is that there is no or minimal electrical contact between the electrodes, i.e. crosstalk is minimal. Yet a further advantage is that such fabric, foam, or tissue can be produced at very low cost.

DETAILED DESCRIPTION OF THE INVENTION

Figure 1:
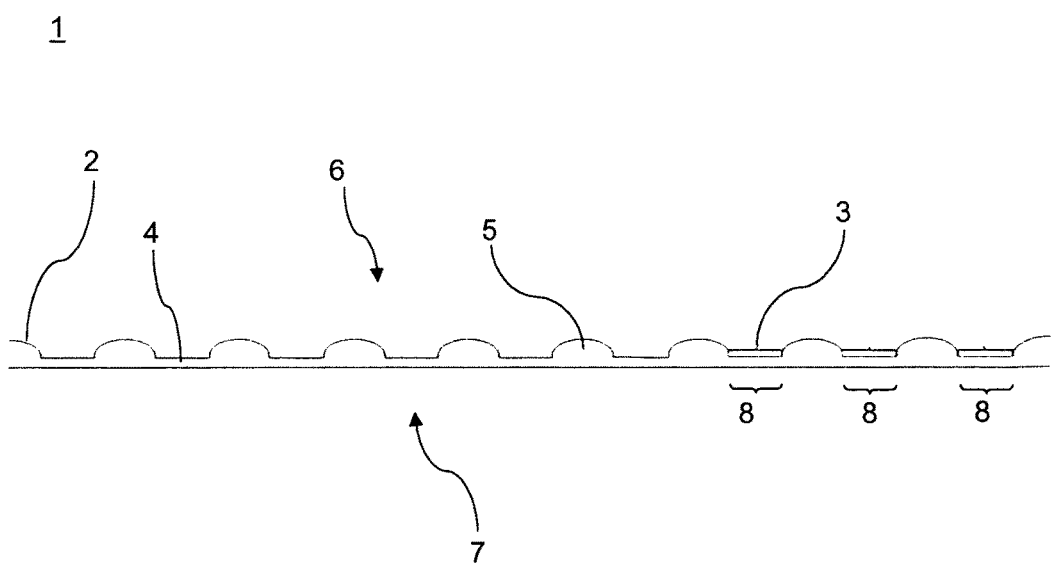
FIG. 1: schematic longitudinal sectional view of an electrode sensor comprising an electrically conductive foam material.

While this invention is susceptible of embodiments in many different forms, there is shown in the drawings and will herein be described in detail, embodiments of the invention with the understanding that the present disclosure is to be considered as an exemplification of the principles of the invention and is not intended to limit the broad aspects of the invention to the embodiments illustrated.

In the longitudinal section view of FIG. 1 is presented a belt-like or strip-like structure 1 comprising an electrically conductive foam material 2 and contact elements 3. The foam material 2 consists for example of a conductive polymer or a polymeric material with conductive inclusions. The foam material is formed into compressed areas 4 and non-compressed areas 5. The compressed areas 4 exhibit an increased density with regard to the non-compressed areas 5. The compressed areas 4 are separated from each other by non-compressed areas 5. Contact elements 3 are situated on the compressed areas 4. A strip of foam 2 is compressed in such a way that on a first side 6 of the strip 1 the compressed areas 4 form indents. The strip of foam 2 is permanently compressed. In the indents contact elements 3 may be positioned. The contact elements 3 connect the dense compressed foam surface with the electronics of a medical instrument, in particular with a current and/or voltage source and/or an analyzing electronic unit. The second or opposite side 7 of the strip essentially forms a flat surface. This second side 7 of the strip 2 is foreseen to contact the skin of a test person or patient. Alternatively, the opposite side 7 may exhibit bumps of compressed foam material (not shown here) for better contact of the belt 1 with the skin. The electrical conductivity of the compressed foam 4 is noticeably higher than the electrical conductivity of the non-compressed foam 5. Not being bound to any theory it is assumed that due to compression fewer foam bubbles obstruct the passage of electrons and/or more and/or wider passageways are accessible for electron transport. Advantageously, the electrical conductivity of the compressed foam 4 is at least two times, at least 10 times, at least 100 times or at least 1000 times higher than the electrical conductivity of the non-compressed foam 5. At the same time the conductivity of the compressed foam 4 is similar to or higher than the conductivity of the skin of a test person or patient. Thus, the resistance of the compressed foam areas 4 is within the range of 1 to 1000 Ohm, or 10 to 100 Ohm. Advantageously the conductivity of the non-compressed foam is lower than the conductivity of the skin. The conductivity of the non-compressed foam is at least 5 times lower than the conductivity of the skin.

Areas 8 of optimal electrical contact between electronics and skin are formed in the belt-like structure opposite the surface side, where the electrical contacts 3 and the compressed foam areas 4 meet. Each area 8 of optimal electrical contact may form an individual electrode. Alternatively, a multitude of neighboring areas 8 of optimal electrical contact may form a compound electrode. The belt-like structure holds a plurality of such individual electrodes or compound electrodes. The individual electrodes or compound electrodes are lined up or arranged in an array-type structure longitudinally following the length of the strip 2. This belt-like structure may serve for electrical impedance tomography (EIT) analysis measurements.

In FIGS. 2(a) and 2(b) is presented a fabric 9 comprising an electrically non-conductive base material 10 and a pattern of electrically conductive material 11. In FIG. 2(a) the fabric 9 is presented schematically in a spaced apart relation to an array of contact elements 15. In FIG. 2(b) fabric 9 and array of contact elements 15 are presented in working position, e.g. a measurement taking position. The non-conductive base material 10 consists of e.g. cotton, felt, carbon fiber or any other natural or synthetic garment material or a mixture thereof. The base material 10 may be a woven or non-woven fabric. The electrically conductive material 11 may consist of yarns, threads or fibers, which comprise metallic material or electrically conductive polymers, or consist of wires. Alternatively, the electrically conductive material 11 may consist of patches of a second material which are integrated into the first material by sewing, stitching or gluing (not shown here). The conductive material 11 is integrated into the base material 10 by stitching, sewing, sputtering, printing, e.g. micro-printing, or was integrated into the base material 10 during the manufacturing process of said base material, e.g. during the weaving or knitting whereby e.g. one of the yarns used comprises conductive material or is a wire or forms a compound material with a wire. Whatever manufacturing method is used it is important that the conductive material 11 forms a multitude of isolated—in the sense of spaced apart—spots, patches or lines on the first surface 12 of the fabric and said spots, patches or lines reach through the thickness of the material to reach and contact the opposite, second surface 13 of the fabric, see FIG. 2(a). Each spot, patch or line on the first surface 12 does hereby form a separate, thus electrically isolated, connection or passageway 14 to the opposite, second garment surface 13. On the first surface 12 electrode contact elements 15 are arranged, each establishing electrical contact to a plurality of electrical passageways 14 leading to the opposite, second surface 13, which in turn establishes physical and electrical contact to the skin 18 of a test person or patient, see FIG. 2(b). Consequently, each electrode contact element 15 contacts the skin electrically via a multitude of isolated spots, patches or lines. Groups of these isolated spots, patches or lines are brought into mutual contact through their common electrode contact element 15 at the opposite side of the fabric 9. Depending on the chosen distance in-between the electrode contact positions 16 or depending on the chosen distribution and patterns of the electrical spots, patches or lines more or less of the interposed electrical pathways 14 are not contacted by any of the electrode contact elements 15. Pathways 14 having no contact to any of the electrode contact elements 15 will not take any functionality during use of the fabric e.g. for EIT measurements. Each electrode contact element 15 may comprise an elaborate electrode chip with various functionalities, such as described in unpublished Swiss patent application Nr. 00364/10, filed on Mar. 16, 2010. The electrode contact elements 15 are connected to each other and to a central control system via a bus system 17. This bus system 17 is insulated against the partially conductive fabric 9.

Figure 3:
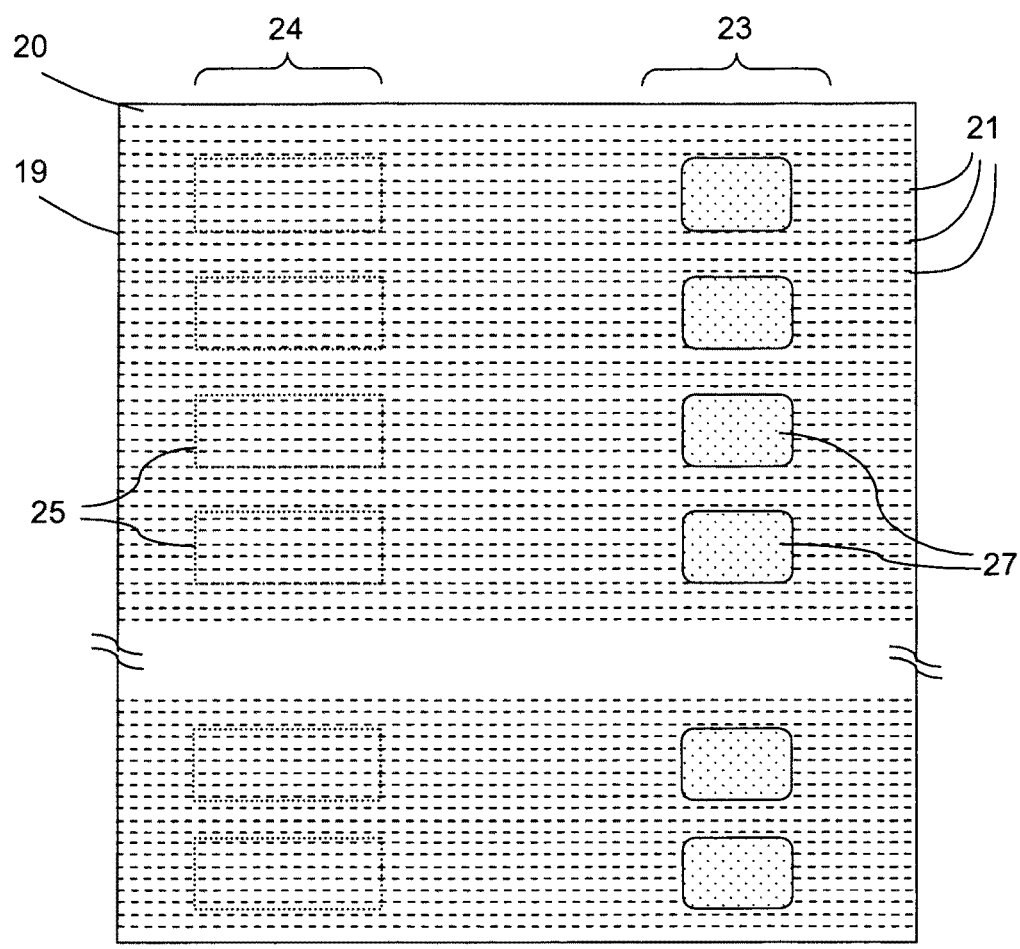
FIG. 3: schematic view of an unfolded electrode sensor comprising a fabric with multiple electrically conducting pathways of a second material.

In FIG. 3 there is presented a patterned carrier material 19 comprising an essentially non-conductive base or carrier material 20 provided with electrical conductive lines 21. The carrier material 19 consists of a non-woven fabric, e.g. of a felt material. Alternatively it may also consist of a woven material, e.g. such as woven yarns comprising any natural or synthetic material or a mixture thereof. A pattern of electrically conductive material is arranged on the surface of the carrier material 20. Said pattern consists of mutually physically spaced apart and electrically non-insulated conductive lines 21 (in FIG. 3 three lines are pointed out exemplarily). The electrically conductive line material 21 may consist of yarns comprising or made of metallic material or electrically conductive polymers, or it may consist of wires. These lines 21 may be integrated into the surface of the carrier material 20 by sewing, stitching, printing, sputtering or gluing. Advantageously, the electrically conductive line material 21 may consist of a conductive paint, which is printed, e.g. by micro-printing, onto the surface of the non-woven or woven fabric. The conductive material forms a multitude of separate lines 21 or separate groups of lines on at least one surface of the fabric, whereby each line or group of lines connects two distant points or areas, respectively, on the base material 20. Individual patches or lines are electrically isolated from each other in such a way that electrical current passing through one line or patch does not interfere with the current passing in another neighboring line or patch. An arrangement of the multitude of isolated lines or groups of lines is a parallel arrangement as shown in FIG. 3. In FIG. 3 electrically conducting lines 21 are arranged on an elongate strip comprising said carrier material 20. The lines 21 cross the width of the strip to connect areas of the left side of the strip with the right side of the strip. Lines 21 lead from a first (patterned) area 23, which is determined to establish in use physical contact with an array of contact elements 27, to a second (patterned) area 24, which is determined to establish in use physical contact with skin. Electrode array elements 27 will be able to establish electrical contact to the skin via those electrical lines 21, which are contacting the elements 27. Consequently electrical contact to the skin will be established at distinct electrical contacting areas 25. Approximately, these electrical contacting areas 25 are indicated in FIG. 3.

Figure 4:
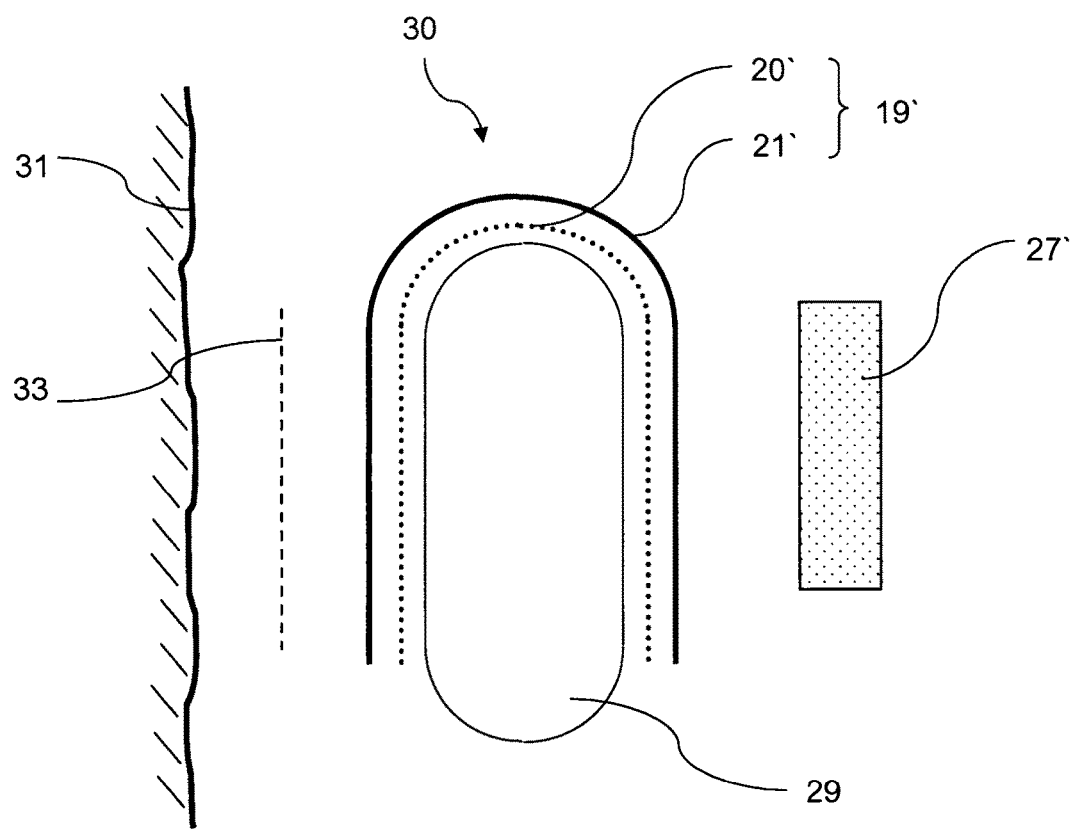
FIG. 4: schematic cross sectional view of an electrode sensor comprising pathways, set in relation to electrical contact element and skin.

In use, as e.g. an EIT electrode, the patterned carrier material 19 may be folded with its patterned side forming the exterior side after the folding. In FIG. 4 a cross section of the folded patterned carrier material 19' is schematically shown. The patterned carrier material 19' comprising the carrier material 20' and the electrical lines 21' is folded around a core material 29 for support. Within the first area 23 electrode contact elements 27 (e.g. EIT chip electrodes) are placed on the patterned carrier material 19, 19', see FIGS. 3 and 4. Electrical conductive lines 21 and 21' which contact the electrode contact elements 27 and 27' establish hereby electrical contact with the skin 31 at the electrical contacting areas 25. The support material 29, shown in FIG. 4, may consist of non-conductive foam or another non-conductive material. Foam core 29 and patterned carrier material 19' form an elongate belt-like interface structure 30 which for use is laid around body parts of a test person or patient. Furthermore, an electrode array with a bus system connecting the numerous electrodes 27, 27' of the array is affixed in contacting arrangement on the electrode contacting side of the belt-like interface structure 30. The electrode array with bus system may be fixedly arranged or integrated on the patterned carrier material 19, 19' or may be attached removably just for the time of use.

In-between the belt-like interface structure 30 and the skin 31 of a test person or patient may be interposed a, thin, continuous contact enhancing material 33, for example a hydrophilic hygroscopic material, e.g. a non-woven material or foam. Layer 33 serves to enhance physical and electrical contact properties between skin 31 and belt-like interface structure 30.

Figure 2:
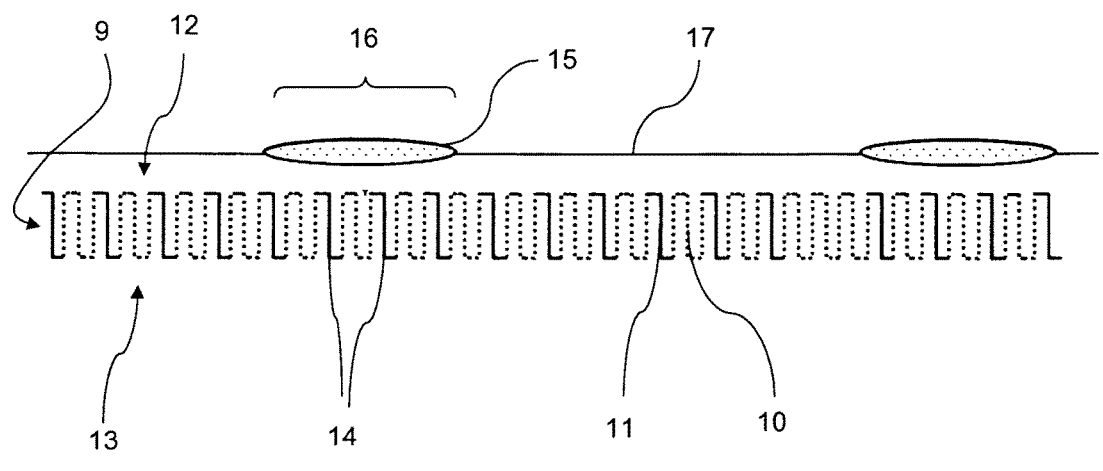
FIG. 2: schematic sectional view of an electrode sensor comprising a fabric with multiple electrically conducting passageways of a second material, (a) array of contact elements and bus system in spaced apart relation, (b) in measuring position.
Figure 2:
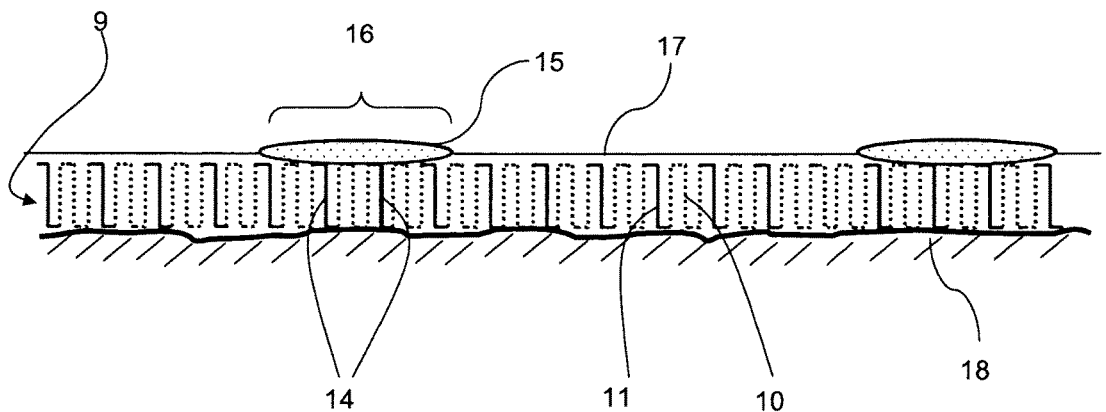
Figure 5:
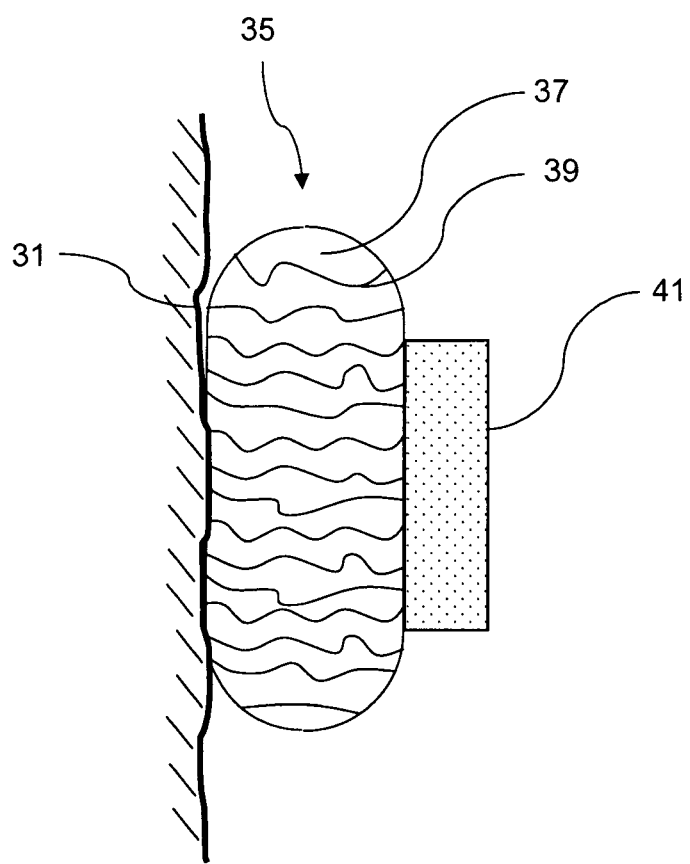
FIG. 5: schematic cross sectional view of an electrode sensor comprising pathways, set in relation to electrical contact element and skin.

In FIG. 5 is schematically shown a cross section of another belt-like interface structure 35. The belt-like interface structure 35 is shown to carry a contact element 41 of an array of contact elements for establishing electrical contact with the skin 31 of a test person (shown in operating position). Here the belt-like structure consists of a carrier material 37 comprising electrical conductive pathways 39. These pathways 39 reach to the surface of the material 37, form there a pattern of electrically conducting material (e.g. point pattern, i.e. an electrically incoherent pattern of points), and allow electrical contact between distinct electrodes 41 and distinct skin surface areas. For better contacting properties the strip crossing pathways 39 may end as small electrical conductive bumps protruding from the surface of the carrier material 37 (not shown here). Additionally or alternatively, a contact enhancing material may be interposed, in particularly between skin 31 and belt-like interface structure 35 (similarly as shown in FIG. 4). Said carrier material 37 comprising electrical conductive pathways 39 for example may be composed of a fabric comprising e.g. electrical conductive yarns (similarly as shown in FIG. 2), of a foam material which forms after compression electrical conductive pathways in the direction of pressure application (similarly as shown in FIG. 1) or of another structure effectively having electrical conductive distinct pathways which allow to contact different skin areas with different contact elements.

Figure 6:
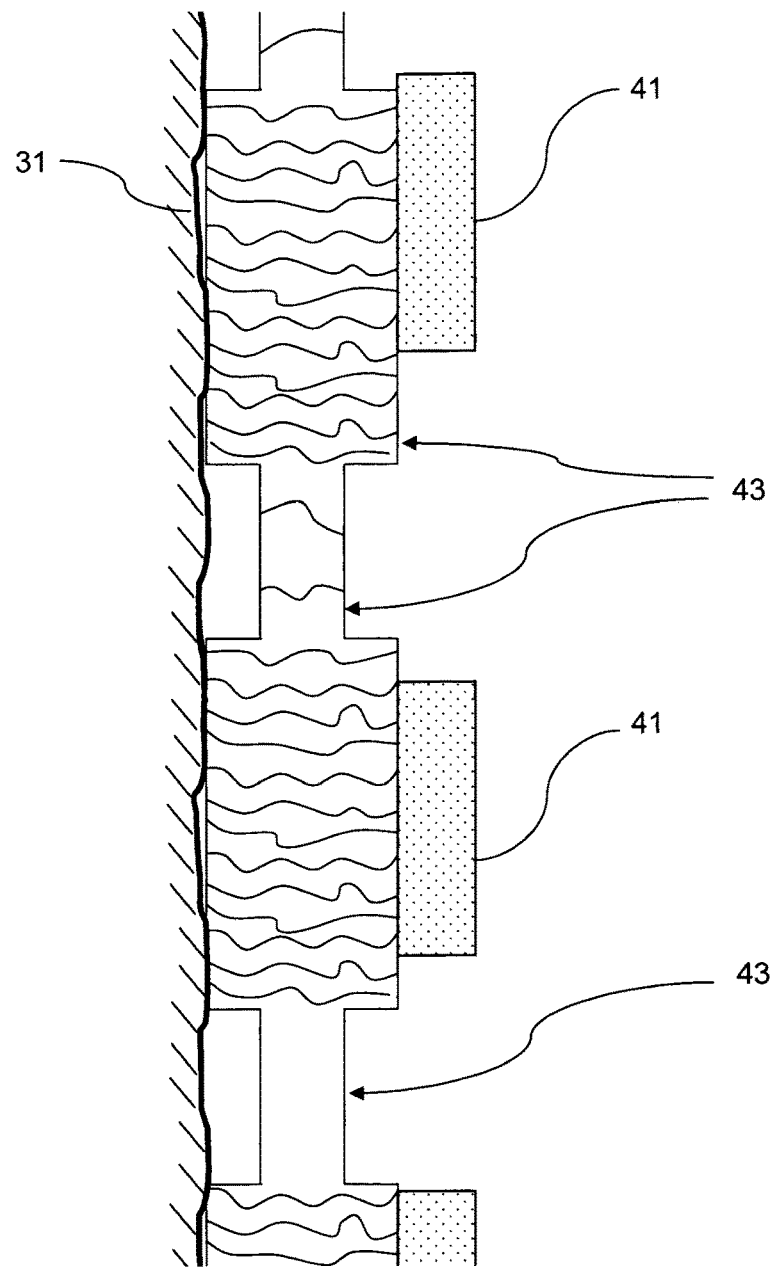
FIG. 6: schematic longitudinal sectional view of an electrode sensor having a rippled interface structure, set in relation to electrical contact elements and skin.

In FIG. 6 is schematically shown a longitudinal section view of another belt-like structure 43 supporting contact elements 41 of an array of contact elements for establishing electrical contact with the skin 31 of a test person (shown in operating position). Here the belt-like structure 43 consists of a similar carrier material comprising electrical conductive pathways as described above with the help of FIG. 5. Differing from the simple belt-like structure shown in FIG. 5, the here displayed belt-like structure 43 has a rippled shape. Hereby regions of higher thickness, i.e. ripples, alternate with regions of lower thickness, i.e. bridges. The ripples are oriented orthogonally with regard to the longitudinal extension of the belt. The bridge structures between the ripples may or may not comprise conductive pathways. Each array electrode contact element 41 may be arranged on top of an individual ripple or alternatively each and/or some of the electrode contact elements may contact several ripples. The position of the contact elements 41 does not have to be precise, as shown in the figure, in order to establish sufficient contact. The rippled structure assists to increase the contact pressure on the skin surface, while at the same time the patient is well cushioned and heat and humidity may dissipate along the tunnels formed in-between skin and belt-like structure at locations where the bridging regions are situated. Moreover, the narrow bridge-like regions operate as electrical insulators because the skin and bridges are spaced apart. Optionally the bridge regions do not contain any electrically conductive pathways. A further effect of the rippled structure is a better stretchability of the belt-like structure and therefore a better adaptation to the body shape.

The location of an effective electrode area on the skin surface is situated approximately below and in the vicinity of the contact element (3, 15, 27, 27', 41), see any of the examples given in FIG. 1-6. Such arrangements can be advantageous and user-friendly, because e.g. the user visually can see and check, where on the body, the skin is electrically contacted (given that the contact elements are actually visible or their location is marked). Moreover such arrangements can be favourable because the distance between contact element and skin is short, which improves for example the accuracy and reliability of the measurements.

The invention claimed is:

1. An electrical impedance tomography imaging system, comprising:
    a processor configured to perform electrical impedance tomography imaging;
    an electrode sensor electrically coupled to the processor, the electrode sensor comprising:
        an array of a plurality of spaced apart contact elements;
        a carrier in the shape of an elongate strip configured for forming contact between the contact elements and skin of a patient,
        wherein the carrier comprises an electrically insulating or poorly electrically conducting material, defining a skin contact surface and defining an array contact surface, the skin contact surface and the array contact surface positioned in different planes; and
        a plurality of electrically conductive lines on the carrier, the plurality of electrically conductive lines forming a pattern of mutually electrically isolated and substantially parallel conductive lines extending across the skin contact surface of the carrier and leading to the array contact surface of the carrier, and the electrically conductive lines being arranged in essentially orthogonal direction to the longitudinal extension of the carrier;
        wherein the spaced apart contact elements of the array are spread along the longitudinal extension of the carrier,
        wherein each contact element comprises a surface area large enough to cover and make electrical contact with a set of at least one but less than all electrically conductive lines when contacting the array contact surface of the carrier, with each contact element being electrically connected to a different set of electrically conductive lines; and
        wherein each contact element and respective set of electrically conductive lines in contact therewith form an individual effective and electrically isolated electrode on the skin contact surface that is electrically isolated from others of the plurality of electrically conductive lines and the plurality of contact elements, respectively.

2. A method of electrical impedance tomography imaging, comprising:
    utilizing a processor configured to perform electrical impedance tomography imaging; and
    coupling an electrode sensor to the processor for one of medical monitoring or measuring an electrical field on a living being, the electrode sensor comprising:
        an array of a plurality of spaced apart contact elements;
        a carrier in the shape of an elongate strip, the carrier configured for forming contact between the plurality of contact elements and skin of a patient, the carrier comprised of an electrically insulating or poorly electrically conducting material defining a skin contact surface and an array contact surface, the skin contact surface and the array contact surface each positioned on opposite sides of the carrier from one another;
        plurality of mutually electrically isolated and substantially parallel conductive lines, said parallel conductive lines extending across the skin contact surface, leading to the array contact surface and being arranged in essentially orthogonal direction to the longitudinal extension of the carrier;
        wherein the spaced apart contact elements of the array are spread along the longitudinal extension of the carrier;
        wherein each contact element comprises a surface area large enough to cover and make electrical contact with a set of at least one but less than all substantially parallel conductive lines when contacting the array contact surface of the carrier, with each contact element being electrically connected to a different set of substantially parallel conductive lines; and
        wherein each contact element and respective set of substantially parallel conductive lines in contact therewith form an individual electrically isolated electrode on the skin contact surface that is electrically isolated from others of the plurality of substantially parallel conductive lines and others of the plurality of contact elements.

3. The electrical impedance tomography imaging system of claim 1, wherein each of the plurality of substantially parallel conductive lines is electrically isolated from one another in such a way that electrical current passing through one of the plurality of substantially parallel conductive lines does not interfere with electrical current passing through another one of the substantially parallel conductive lines.

4. The electrical impedance tomography imaging system of claim 1, wherein each of the plurality of spaced apart contact elements is detachably fixable to the skin contact surface.

5. The electrical impedance tomography imaging system of claim 1, wherein a first and a second part of each of the plurality of substantially parallel conductive lines are each substantially positioned on opposite sides of the carrier from one another.

6. The electrical impedance tomography imaging system of claim 1, wherein the plurality of substantially parallel conductive lines are arranged so that when one of the plurality of contact elements contacts the carrier in an area of contact on the array contact surface the area essentially defines an individual electrically isolated electrode on the skin contact surface of the carrier.

7. The electrical impedance tomography imaging system of claim 1, wherein the plurality of substantially parallel conductive lines extend around a lateral edge of the carrier.

8. The electrical impedance tomography imaging system of claim 7, wherein the plurality of substantially parallel conductive lines is integral with the carrier.

9. The electrical impedance tomography imaging system of claim 1, wherein each of the plurality of substantially parallel conductive lines is mounted to a support structure.

10. The electrical impedance tomography imaging system of claim 9, wherein the support structure comprises a flexible belt-like structure.

11. The electrical impedance tomography imaging system of claim 1, wherein the carrier comprises at least one of foam or woven, knitted, non-woven or spacer fabric.

12. The electrical impedance tomography imaging system of claim 1, wherein the plurality of substantially parallel conductive lines comprises at least one of electrically conductive paint or electrically conductive particulate material.

13. The electrical impedance tomography imaging system of claim 12, wherein the at least one of electrically conductive paint or electrically conductive particulate material is sputtered or printed on the carrier.

14. The electrical impedance tomography imaging system of claim 12, wherein the at least one of electrically conductive paint or electrically conductive particulate material is deposited by micro-printing on the carrier.

15. The electrical impedance tomography imaging system of claim 1, wherein the plurality of substantially parallel conductive lines comprises at least one of electrically conductive yarn, wire or fibers woven, knitted or stitched into an electrically insulating or poorly electrically conducting fabric.

16. The electrical impedance tomography imaging system of claim 1, wherein the carrier is formed from an elongate strip, wherein the plurality of substantially parallel conductive lines are arranged in essentially orthogonal direction to the longitudinal extension of the elongate strip and the plurality of contact elements are spread along a longitudinal extension of the elongate strip.

17. The electrical impedance tomography imaging system of claim 1, wherein the carrier comprises the skin contact surface on one side and the array contact surface on an opposite side thereof.

18. The electrical impedance tomography imaging system of claim 9, wherein the support structure and the carrier are fixedly joined.

19. The electrical impedance tomography imaging system of claim 18, wherein the support structure and the carrier are fixedly joined by a heat-sealed connection.

20. The electrical impedance tomography imaging system of claim 9, wherein the support structure and the carrier are releasably fastened to one other.

21. The electrical impedance tomography imaging system of claim 20, wherein the support structure and the carrier are releasably fastened to one other by a hook-and-loop tape.

22. The electrical impedance tomography imaging system of claim 16, wherein the elongate strip is folded to form a fold therein and the plurality of substantially parallel conductive lines extending around a lateral edge formed by the fold.

23. The method of electrical impedance tomography imaging of claim 2, further comprising coupling the electrode sensor to the processor wherein each of the plurality of substantially parallel conductive lines of the electrode sensor is electrically isolated from one other in such a way that electrical current passing through one of the plurality of substantially parallel conductive lines does not interfere with electrical current passing through another one of the plurality of substantially parallel conductive lines.

24. The method of electrical impedance tomography imaging of claim 2, further comprising coupling the electrode sensor wherein each of the plurality of spaced apart contact elements of the electrode sensor is detachably fixable to the skin contact surface.

25. The method of electrical impedance tomography imaging of claim 24, further comprising coupling the electrode sensor wherein each of the plurality of conductive lines of the electrode sensor comprise two parts that are each substantially positioned on opposite sides of the carrier from one another.

26. The method of electrical impedance tomography imaging of claim 2, further comprising coupling the electrode sensor wherein each of the plurality of spaced apart contact elements of the electrode sensor is detachably fixable to the skin contact surface.

27. The method of electrical impedance tomography imaging of claim 2, further comprising coupling the electrode sensor wherein a first and a second part of each of the plurality of substantially parallel conductive lines of the electrode sensor are each substantially positioned on opposite sides of the carrier from one another.

28. The method of electrical impedance tomography imaging of claim 2, further comprising coupling the electrode sensor wherein the plurality of substantially parallel conductive lines of the electrode sensor are arranged so that when one of the plurality of contact elements contacts the carrier in an area of contact on the array contact surface the area essentially defines an individual electrically isolated electrode on the skin contact surface of the carrier.

29. The method of electrical impedance tomography imaging of claim 2, further comprising coupling the electrode sensor wherein the plurality of substantially parallel conductive lines of the electrode sensor extend around a lateral edge of the carrier.

30. The method of electrical impedance tomography imaging of claim 29, further comprising coupling the electrode sensor wherein the plurality of substantially parallel conductive lines of the electrode sensor is integral with the carrier.

31. The method of electrical impedance tomography imaging of claim 2, further comprising coupling the electrode sensor wherein each of the plurality of substantially parallel conductive lines of the electrode sensor is mounted to a support structure.

32. The method of electrical impedance tomography imaging of claim 31, further comprising coupling the electrode sensor wherein the support structure of the electrode sensor comprises a flexible belt-like structure.

33. The method of electrical impedance tomography imaging of claim 2, further comprising coupling the electrode sensor wherein the carrier of the electrode sensor comprises at least one of foam or woven, knitted, nonwoven or spacer fabric.

34. The method of electrical impedance tomography imaging of claim 2, further comprising coupling the electrode sensor wherein the plurality of substantially parallel conductive lines of the electrode sensor comprises at least one of electrically conductive paint or electrically conductive particulate material.

35. The method of electrical impedance tomography imaging of claim 34, further comprising coupling the electrode sensor wherein the at least one of electrically conductive paint or electrically conductive particulate material of the electrode sensor is sputtered or printed on the carrier.

36. The method of electrical impedance tomography imaging of claim 34, further comprising coupling the electrode sensor wherein the at least one of electrically conductive paint or electrically conductive particulate material of the electrode sensor is deposited by micro-printing on the carrier.

37. The method of electrical impedance tomography imaging of claim 2, further comprising coupling the electrode sensor wherein the plurality of substantially parallel conductive lines of the electrode sensor comprises at least one of electrically conductive yarn, wire or fibers woven, knitted or stitched into an electrically insulating or poorly electrically conducting fabric.

38. The method of electrical impedance tomography imaging of claim 2, further comprising coupling the electrode sensor wherein the carrier of the electrode sensor is formed from an elongate strip, wherein the plurality of substantially parallel conductive lines are arranged in essentially orthogonal direction to the longitudinal extension of the elongate strip and the plurality of contact elements are spread along a longitudinal extension of the elongate strip.

39. The method of electrical impedance tomography imaging of claim 32, further comprising coupling the electrode sensor wherein the support structure and the carrier of the electrode sensor are fixedly joined.

40. The method of electrical impedance tomography imaging of claim 39, further comprising coupling the electrode sensor wherein the support structure and the carrier of the electrode sensor are fixedly joined by a heat-sealed connection.

41. The method of electrical impedance tomography imaging of claim 32, further comprising coupling the electrode sensor wherein the support structure and the carrier of the electrode sensor are releasably fastened to one other.

42. The method of electrical impedance tomography imaging of claim 41, further comprising coupling the electrode sensor wherein the support structure and the carrier of the electrode sensor are releasably fastened to one other by a hook-and-loop tape.

43. The method of electrical impedance tomography imaging of claim 38, further comprising coupling the electrode sensor wherein the elongate strip of the electrode sensor is folded to form a fold therein and the plurality of substantially parallel conductive lines extending around a lateral edge formed by the fold.

* * * * *